United States Patent [19]

Hu

[11] Patent Number: 5,784,481

[45] Date of Patent: Jul. 21, 1998

[54] CT CONE BEAM IMAGE RECONSTRUCTION WITH CIRCLE AND LINE SCAN PATH

[75] Inventor: Hui Hu, Waukesha, Wis.

[73] Assignee: General Electric Company, Milwaukee, Wis.

[21] Appl. No.: 673,453

[22] Filed: Jun. 25, 1996

[51] Int. Cl.$^6$ ........................................... G06K 9/00

[52] U.S. Cl. .................. 382/131; 378/4; 378/901

[58] Field of Search ........................... 382/131; 378/4, 378/14, 26, 131, 901

[56] References Cited

U.S. PATENT DOCUMENTS

| | | | |
|---|---|---|---|
| 5,170,439 | 12/1992 | Zeng et al. | 382/6 |
| 5,400,255 | 3/1995 | Hu | 364/413.19 |
| 5,404,293 | 4/1995 | Weng et al. | 382/131 |

OTHER PUBLICATIONS

"Practical cone–beam algorithm" Feldkamp et al. *J. Opt. Soc. Am. A*/vol. 1, No. 6/Jun. 1984; pp. 612–619.

"A New Cone Beam Reconstruction Algorithm for the Circular Orbit," H.Hu.IEEE MIC 1994;pp. 1261–1265.

Primary Examiner—Jose L. Couso
Assistant Examiner—Matthew C. Bella
Attorney, Agent, or Firm—James O. Skarsten; John H. Pilarski

[57] ABSTRACT

A CT cone beam imaging system is provided wherein a source of cone beam radiation and a detector array are mounted for movement with respect to an object, to provide a reconstructed image of the object. Relative movement is established between the cone beam source and the object along a scan path comprising a circular component and a linear component. The source is operated to irradiate the object during such movement to project cone beam data onto the detector, the projected data comprising linear and circular data sets which respectively correspond to the linear and circular components of the scan path. To significantly minimize processing requirements, a subset of data elements is selected from the linear data set, wherein each of the selected data elements is associated with a set of spatial parameters which define spatial regions contained within a hypothetical sphere in the Radon space, but which are not intersected by a Radon shell defined by dimensions of the circular path and the cone beam. First and second sets of image reconstruction data are respectively generated from the subset of the linear data and the circular data, the first and second sets being combined to provide an image of the object.

9 Claims, 3 Drawing Sheets

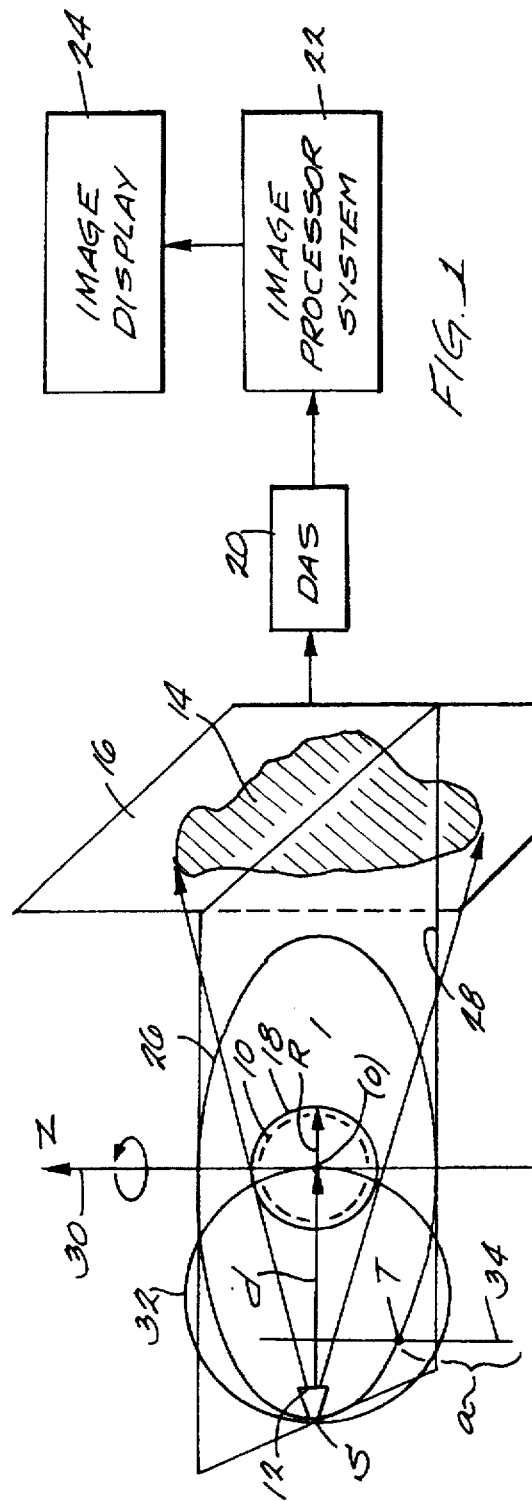
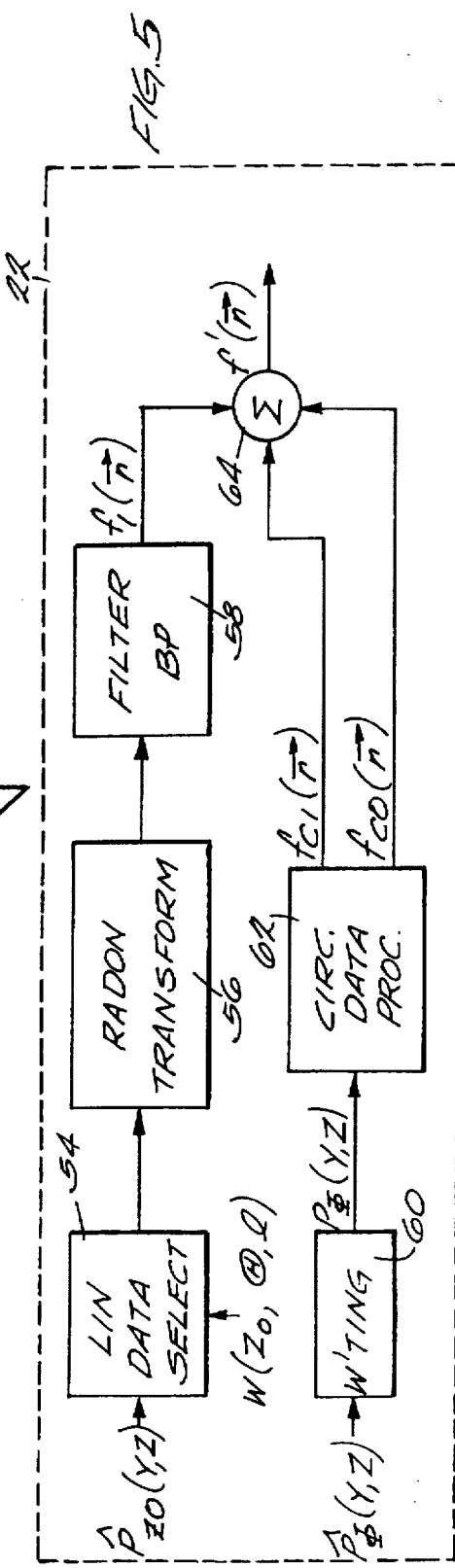

CT CONE BEAM IMAGE RECONSTRUCTION WITH CIRCLE AND LINE SCAN PATH

BACKGROUND OF THE INVENTION

The invention disclosed and claimed herein generally pertains to method and apparatus for significantly improving accuracy and efficiency in computed tomography (CT) cone beam image reconstruction. More particularly, the invention pertains to such method and apparatus wherein the cone beam scans along a circle and line trajectory in order to acquire data.

Cone beam imaging has developed as an important technique in constructing a CT image of an object, and in particular a three-dimensional CT image. According to such technique, a cone beam x-ray source irradiates the object while traversing a prescribed orbit or trajectory, to project an image of the object, in the form of cone beam x-ray data, onto an array of detector elements. The detector elements acquire or receive the projected cone beam data, which is then processed to provide the image.

Scan path geometry is an essential consideration in cone beam imaging. It would be desirable, from a standpoint of simplification and symmetry, to scan along a trajectory comprising a circular orbit lying in a single plane. However, it is well known that such orbit is likely to provide insufficient cone beam data for exact image reconstruction. This has been shown, for example, in an article by Smith entitled "Image Reconstruction from Cone-Beam Projections: Necessary and Sufficient Conditions and Reconstruction Methods," IEEE Trans. Med. Image, Vol. MI-4, 14–28 (1985). This article also sets forth a cone beam data sufficiency criterion.

Various scanning geometries have been developed to ensure that the sufficiency criterion of Smith is complied with. In one such geometry, the scan path comprises a circular orbit in combination with a linear path, which is orthogonal to the plane of the circular orbit. Such combination scan path is of great practical interest, since it can be readily implemented by means of a conventional CT gantry configuration. Various algorithms are currently available for use in processing cone beam data acquired by scanning along a combined circle and line path, and constructing an image therefrom. However, one of such algorithms is of the shift-variant filtering back projection form, which is comparatively difficult to implement in practice. Other of such algorithms have been found to contain artifacts, and are not sufficiently exact or accurate. Still other algorithms require excessive data processing steps, resulting in inefficient image reconstruction.

SUMMARY OF THE INVENTION

In a CT imaging system, or other arrangement wherein a source of cone beam radiation, together with a planar detector array, are mounted for selective movement with respect to an object, a method is provided for reconstructing an image of the object from acquired projected data. The method includes the step of moving the cone beam source, relative to the object, along a scan path comprising a circular orbit and a linear path. The cone beam source irradiates the object during such movement to project cone beam data onto the detector plane, the projected data comprising a linear data set and a circular data set which respectively correspond to the linear and circular components of the scan path. The method further includes the step of selecting a subset of data elements from the linear data set, each of the selected data elements being associated with a specified set of spatial parameters. A Radon transform is applied to each data element in the selected subset to provide a first set of image reconstruction data. A second set of image reconstruction data is generated from the circular data set, and the first and second sets of image reconstruction data are combined to provide an image of the object.

In a preferred embodiment, the specified spatial parameters define spatial regions which are contained within a hypothetical sphere enclosing the object, and which are not intersected by any Radon shell defined by the dimensions of the circular path and the cone beam. Preferably also, the first and second sets of image reconstruction data are generated by processes which include filtering and back projecting the cone beam data.

OBJECTS OF THE INVENTION

An object of the invention is to improve accuracy and efficiency in providing an image of an object, wherein imaging data is acquired by irradiating the object with a cone beam source.

Another object is to provide a method and apparatus for improving efficiency in cone beam image reconstruction by selectively reducing the amount of data, acquired during the linear portion of a circle and line scan path, which must be Radon transformed or otherwise processed.

These and other objects of the invention will become more readily apparent from the ensuing specification, taken together with the accompanying drawings.

BRIEF DESCRIPTION OF THE DRAWINGS

FIG. 1 is a schematic diagram illustrating principal elements of a CT cone beam imaging system and an associated circle-and-line scan path.

FIG. 5 is a block diagram showing a processor for use in implementing an embodiment of the invention.

DETAILED DESCRIPTION OF THE PREFERRED EMBODIMENT

Figure 3:
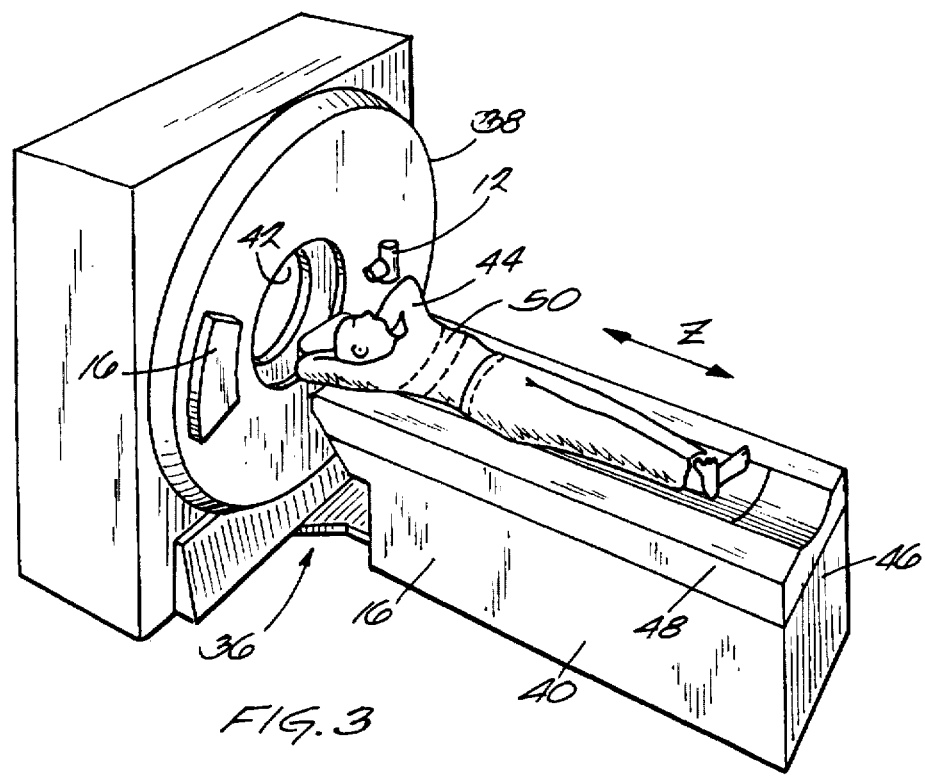
FIG. 3 is a perspective view further illustrating a conventional CT imaging system for use in implementing an embodiment of the invention.

Referring to FIG. 1, there are shown the principal components of a cone-beam imaging system for reconstructing and displaying an image of an object 10 contained within a hypothetical spherical volume 18 of radius R. A cone beam x-ray source 12 is positioned to irradiate object 10, and to thereby project cone-beam data representing an image 14 thereof onto an associated planar detector array 16, comprising a matrix array of discrete detector elements (not shown in detail). The cone-beam projection data is in the form of x-ray photons that penetrate the object and are sensed by the respective detector elements, of detector array 16. Thus, planar detector 16 provides cone beam projection data in analog form. Such data is coupled to a Data Acquisition System (DAS) 20, which samples analog data from the respective detector elements and converts the data to digital form for subsequent processing. The digitized projection data is coupled to an image reconstruction processor system 22, which operates on the projection data in accordance with the invention, as described hereinafter, to reconstruct an image of the object 10. The reconstructed image may be presented in viewable form, for example, by means of an image display 24.

FIG. 1 further shows a circular orbit of motion 26 for the cone beam source 12 around the object 10, such orbit lying in a mid-plane 28, i.e. a plane passing through the center of sphere 18. In a typical arrangement, detector array 16 is constrained to move with source 12, so that object 10 remains positioned therebetween. Cone-beam projection data is acquired by detector array 16 for successive positions or view angles of source 12, as source 12 traverses the circular orbit 26. A Z-axis 30 passes through the object 14, in orthogonal relationship with mid-plane 28, and intersects the mid-plane at a point 0, the center of spherical volume 18. The point 0 is usefully selected as the origin for coordinate systems in both Radon and object space.

FIG. 1 further shows the Radon shell 32 when the source 12 is located at a position S along the circular orbit 26. As is well known to those of skill in the art, the Radon shell is a spherical shell having a diameter d equal to the distance between the origin O and the source position S. As source 12 traverses around circular orbit 26, the Radon shells 32 for all view positions collectively define or describe a toroidal shaped space or volume.

Figure 2:
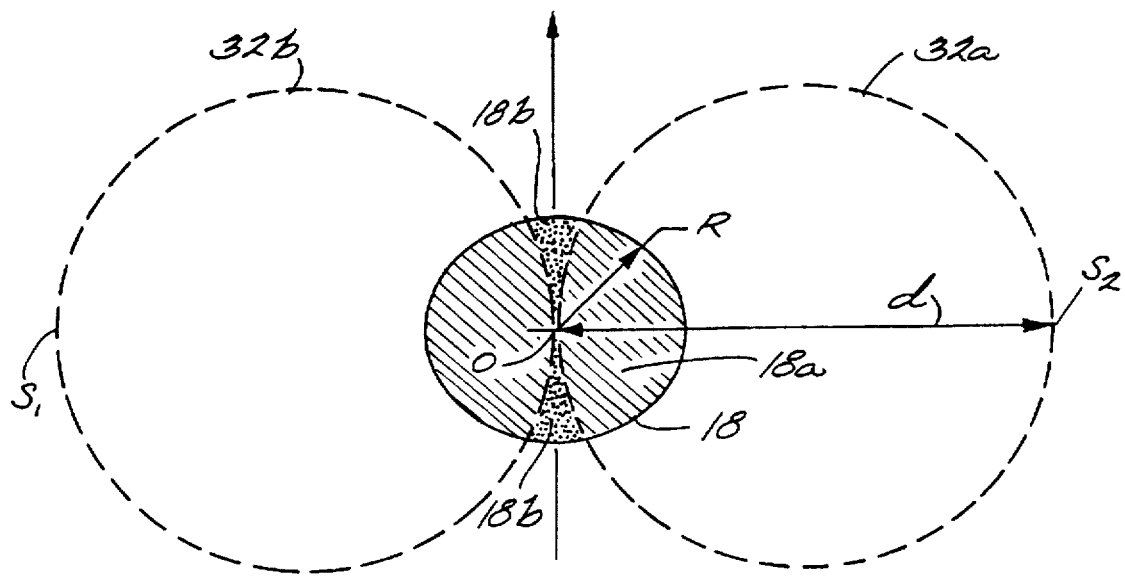
FIG. 2 is a view of Radon space illustrating spatial regions, within a spherical volume enclosing an object to be imaged, which are supported by cone beam projection data acquired over the circular and linear portions, respectively, of the scan path shown in FIG. 1.

Referring to FIG. 2, it will be seen that such toroidal space intersects a spatial region 18a of the space enclosed by spherical volume 18, but does not intersect spatial region 18b thereof. FIG. 2 shows sections of Radon shells 32a and 32b, which respectively show the Radon shell 32 for two different view positions $S_1$ and $S_2$ which are separated by 180 degrees. For simplification source 12 and object 10 are not shown in FIG. 2.

As is further well known in the art, if a component of object 10 is associated with a spatial region 18a of spherical volume 18 in the Radon space, it can be exactly reconstructed from cone beam projection data, hereinafter referred to as circular projection data, which has been acquired as source 12 moves around the circular orbit 26. However, such circular projection data cannot produce the reconstruction of the component of object 10 associated with a spatial region 18b of spherical volume 18 in the Radon space. Accordingly, additional cone beam projection data, hereinafter referred to as linear projection data, is acquired by further moving source 12 along a linear orbit path 34, shown in FIG. 1. Linear path 34 is tangent to the circular orbit 26 at a point T, and is oriented in orthogonal relationship with the plane of circular orbit 26 and mid-plane 28. Moreover, linear path 34 has a length of 2a and is bisected by midplane 28, where the half-length a is selected to be greater than or equal to the quantity $2dR/\sqrt{d^2-R^2}$. By providing such length for the linear path 34, the sufficiency condition will be met. That is, the linear projection data acquired by scanning source 12 over the linear path 34 can be used to reconstruct the component of object 10 associated with a spatial region 18b of sphere 18 in the Radon space. Thus, a scan path comprising circular orbit 26 and linear path 34 together is the complete and sufficient scan path.

As stated above, such scan path can be readily implemented by a conventional CT system. Referring to FIG. 3, there is shown a conventional CT system substantially comprising a gantry 38 and a table 40. Gantry 38 is provided with a bore 42, and table 40 supports a patient 44 for imaging. Table 40 comprises a base 46, and a patient support member 48 which is slideable upon base 46 to move the patient linearly, along the Z-axis. Thus, table 40 can be operated to insert the patient through the bore 42 to position a selected section 50 of the patient within the bore, so that an image can be taken therethrough. An object 14 may thus comprise a patient section 50.

Referring further to FIG. 3, there is shown a source 12 and detector array 16 mounted on rotatable gantry 38, on opposing sides of the bore 42. Accordingly, a circular orbit 26, as described above, may be established by selective rotation of gantry 38. A linear path 34 may be established by linear movement of the patient support member 48, while source 12 and array 16 remain stationary. Alternatively, the linear path could be established by mounting the gantry for transitional movement along the Z-axis.

Commonly assigned U.S. Pat. No. 5,400,255, issued Mar. 21, 1995 to Hui Hu, the inventor herein, discloses a technique for reconstructing an image from cone beam projection data acquired over a circular orbit only. Such patent taught that an image function $f(\vec{r})$ could be expressed as the sum of two terms, a term $f_c(\vec{r})$ which was supported by the circular projection data, and another term which was not supported thereby. Accordingly, the unsupported term comprised an estimation. Now, however, by means of the invention as disclosed herein, a term $f_1(\vec{r})$ can be generated from the linear projection data. This term may be employed to reconstruct an image from the function $f'(\vec{r})$, where $f'(\vec{r}) = f_c(\vec{r}) + f_1(\vec{r})$. Such image will be significantly more accurate and exact than an image formed in accordance with a prior art technique, wherein portions of the imaged object were not supported by acquired data.

Figure 4:
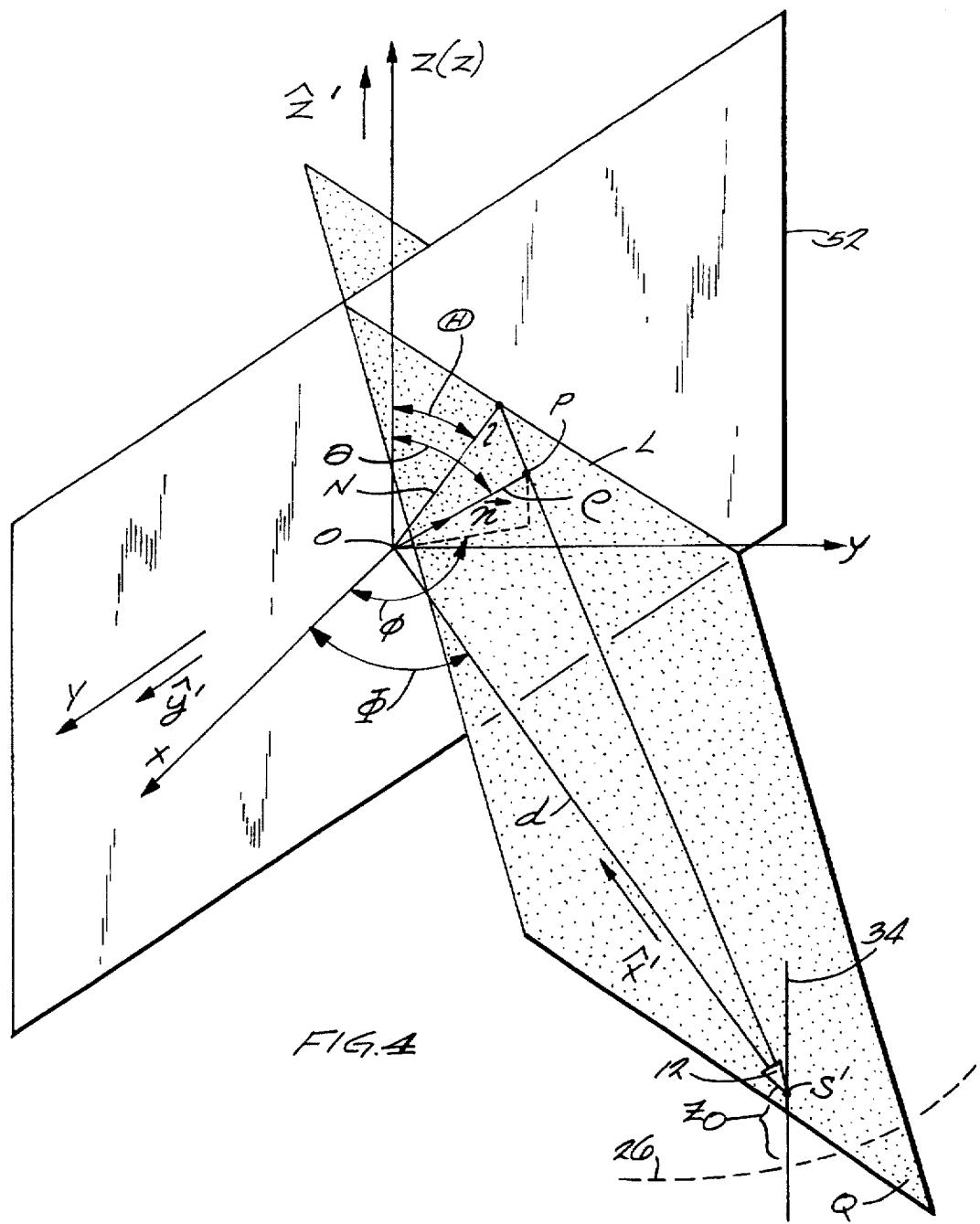
FIG. 4 is a view showing a cone beam imaging arrangement with associated coordinate systems and spatial parameters imposed thereon for use in further illustrating an embodiment of the invention.

Referring to FIG. 4, there is shown a detector array 52 which is similar or identical to array 16. However, for simplicity detector 52 is disposed so that the origin O and Z-axis lie in the detector plane thereof. The relationships developed herein in connection with detector 52 can be readily converted for use with a detector such as planar detector array 16 or the like, which is spaced apart from the origin O and Z-axis, by means of a mapping process. FIG. 4 further shows X- and Y-coordinate axes which are orthogonal to the Z-axis and to one another. Cone beam source 12 is also shown to be located at a position S' along its circle-and line-path. For linear scan, the position of the x-ray source is categorized by $z_0$ along the Z-axis. For circular scan the x-ray source position is identified by the rotational angle Φ. It will be readily apparent that $z_0$ will have a non-zero value only when cone beam source 12 is positioned along the linear path 34 above or below midplane 28.

Since cone beam source 12 both rotates and translates, it is useful to provide an additional moving coordinate system comprising orthogonal vectors $\hat{x}'$, $\hat{y}'$, and $z'$, where $\hat{x}'$ and $\hat{z}'$ are directed along the line S'O and the axis of rotation, i.e., the Z-axis, respectively. Accordingly, $\hat{y}'$ and $\hat{z}'$ lie in the plane of detector 52, and any position therein is identified by the coordinates (Y,Z) with respect thereto. Thus, when source 12 irradiates object 10 from the position $z_0$ on the linear path 34, the detector element at the position (Y,Z) on the detector plane senses or measures a projected linear element $\hat{P}_{zo}(Y,Z)$.

Referring further to FIG. 4, there is shown a point P located on the object 10 (object 10 otherwise not shown in FIG. 4) wherein the location of point P is given by spherical coordinates ($\rho$, $\phi$, $\theta$). $\rho$ is the distance of P from origin O, and $\phi$ and $\theta$ are angles measured from the X- and Z-axes, respectively, to $\vec{n}$, a line normal to line S'P extending from the origin. When source 12 projects x-ray radiation onto object 10 from the position S', a plane Q, which includes point P and source position S', intersects the plane of detector 52 along a line L The line L is usefully defined by coordinates (l, $\Theta$), where l is the length of the line N, comprising a line normal to line L which intersects the origin O. $\Theta$ is the angle between N and the Z-axis. A line integral may be determined by summing the projected data $\hat{P}_{zo}(Y,Z)$ at each (Y,Z) position along the line L. A two dimensional Radon transform may be applied thereto, according to the following relation:

$$\Sigma_{zo}(l,\Theta) = \int\int \frac{d}{\sqrt{d^2+Y^2+Z^2}} \hat{P}_{zo}(Y,Z)\delta(Y\sin\Theta + Z\cos\Theta - l)dY\,dZ \quad \text{Equation 1}$$

As stated above, it is desired to significantly increase efficiency, as well as accuracy, in image reconstruction. This is achieved by minimizing the amount of projection data to which the Radon transform of Equation 1 must be applied. The computational and processing burdens may thereby be significantly reduced. Accordingly, a selection function $w(z_0, \Theta, l)$ is developed as follows:

$$w(z_0,\Theta,l) = 1 \text{ when } 2lz_0\cos\Theta + \omega^2\cos^2\Theta - d^2\sin^2\Theta > 0, \quad \text{Equation 2}$$
$$= 0 \text{ when } 2lz_0\cos\Theta + \omega^2\cos^2\Theta - d^2\sin^2\Theta \leq 0$$

The selection function $w(z_0, \Theta, l)$ is non-zero only for the spatial coordinate position $(z_0, \Theta, l)$ which lie in the regions 18b shown in FIG. 2. These are the only regions from which linear projection data is needed. Accordingly, the spatial selection function of Equation 2 eliminates the need for redundant processing of data. Such selection function is used to provide a function of only the needed coordinate positions $(z_0, \Theta, l)$ as follows:

$$H(z_0,\Theta,l) = \quad \text{Equation 3}$$

$$\cos\Theta w(z_0,\Theta,l)\left(\frac{d^2+l^2}{d^2}\frac{\partial^2\Sigma_{z_0}(l,\Theta)}{\partial^2 l} + \frac{2l}{d^2}\frac{\partial\Sigma_{z_0}(l,\Theta)}{\partial l}\right)$$

From Equation 3, the image reconstruction term $f_1(\vec{r})$ is then determined by integrating over $z_0$ and $\Theta$ as follows:

$$f_1(\vec{r}) = \quad \text{Equation 4}$$

$$-\frac{1}{4\pi^2(d+\vec{r}\cdot\hat{x}')}\int dz_0 \int_{\Theta=0}^{\pi} d\Theta H(z_0,\Theta,l=Y_0\sin\Theta+z_0\cos\Theta)$$

Equation 4 defines a filtered-back projection process. Such process is conventional and well-known to those of skill in the art of CT image reconstruction.

When source 12 irradiates object 10 from a position on circular orbit 26 identified by some angle $\Phi$, the detector element at the position (Y,Z) on the detector plane measures a projected circular data element $\hat{P}_{\Phi}(Y,Z)$. The function $f_c(\vec{r})$ can be readily determined from respective $\hat{P}_{\Phi}(Y,Z)$ by means of a prior art technique, such as the technique disclosed in U.S. Pat. No. 5,400,255, and also in an article by H. Hu entitled "A New Cone Beam Reconstruction Algorithm for the Circular Orbit," IEEE MIC, 1261,1265 (1994).

In accordance with such technique, the function $f_c(r)$ is treated as the sum of image reconstruction functions $f_{c1}(\vec{r})$ and $f_{c0}(\vec{r})$, i.e., $f_c(\vec{r})=f_{c1}(\vec{r})+f_{c0}(\vec{r})$.

$f_{c1}(\vec{r})$ may be determined in accordance with the following equations:

$$P_\phi(Y,Z) = \frac{d}{\sqrt{d^2+Y^2+Z^2}}\hat{P}_\phi(Y,Z) \quad \text{Equation 5}$$

$$\sigma_\phi(Z) = \int P_\phi(Y,Z)dY \quad \text{Equation 6}$$

$$p1_\phi(Z) = \frac{1}{2\pi}\frac{\partial\sigma_\phi(Z)}{\partial Z} = \int dZ' h1(Z-Z')\sigma_\phi(Z') \quad \text{Equation 7}$$

$$f_{c1}(\vec{r}) = -\frac{1}{2\pi}\oint d\Phi \frac{z}{(d+\vec{r}\cdot\hat{x}')^2} p1_\phi[Z(\vec{r})] \quad \text{Equation 8}$$

where: $h1(Z) = \int d\omega j\omega e^{j2\pi\omega Y} \quad \text{Equation 9}$ $$z(\vec{r}) = \frac{dz}{d+\vec{r}\cdot\hat{x}'} \quad \text{Equation 10}$$

Based on Equations 5–10, the $f_{c1}(\vec{r})$ reconstruction can be computed in the following four steps:

1. Multiply each cone beam projection $\hat{P}_\Phi(Y,Z)$ by a weighting factor to get the weighted projection $P_\Phi(Y,Z)$, as shown in Equation 5.

2. Sum the (2D) weighted projection $P_\Phi(Y,Z)$ along the row (the Y) direction, as shown in Equation 6 to get the (1D) row sum $\sigma_\Phi(Z)$.

3. Filter the row sum $\sigma_\Phi(Z)$ by 1D filter $jw_z$, as shown in Equations 7 and 9, to get the filtered row sum $p1\Phi(Z)$. This step can also be accomplished by directly differentiating the row sum $\sigma_\Phi(Z)$, as shown in Equation 7.

4. The filtered row sum $p1_\Phi(Z)$ from each projection is weighted by a position-dependent factor and then backprojected, as shown in Equation 8 to form the $f_{c1}(\vec{r})$ reconstruction.

An algorithm for determining the reconstruction term $f_{c0}(\vec{r})$ is also set forth in an article by Feldkamp et al, entitled "Practical Cone-beam Algorithms," J. Opt. Soc. Am., pp. 612–619(1984).

$$P_\phi(Y,Z) = \frac{d}{\sqrt{d^2+Y^2+Z^2}}\hat{P}_\phi(Y,Z) \quad \text{Equation 11}$$

$$p0_\phi(Y,Z) = \int dY' h(Y-Y')P_\phi(Y',Z) \quad \text{Equation 12}$$

$$f_{c0}(\vec{r}) = \frac{1}{2}\oint d\Phi \frac{d^2}{(d+\vec{r}\cdot\hat{x}')^2} p0_\phi[Y(\vec{r}),Z(\vec{r})] \quad \text{Equation 13}$$

where: $h(Y) = \int d\omega |\omega| e^{j2\pi\omega Y} \quad \text{Equation 14}$ $$Y(\vec{r}) = \frac{d\vec{r}\cdot\hat{y}'}{d+\vec{r}\cdot\hat{x}'} \quad \text{Equation 15}$$

$$Z(\vec{r}) = \frac{dz}{d+\vec{r}\cdot\hat{x}'} \quad \text{Equation 16}$$

Referring to FIG. 5, there are shown certain operations performed in image processing system 22, in accordance with the above equations. Linear data elements $\hat{P}_{zo}(Y,Z)$ are coupled to a linear data selection block 54. Block 54 selects only data elements corresponding to spatial positions $(Z_0, \Theta, l)$ for which the selection function $w(z_0, \Theta, l)$ is non-zero, in accordance with Equation 2. Selected data elements are applied to process block 56, which performs a Radon transform operation as set forth in Equation 1. The outputs of Radon Transform block 56 are applied to filtered-back projection process block 58, which provides the image reconstruction term $f_i(\vec{r})$ in accordance with Equation 4.

Referring further to FIG. 5, there are shown circular data elements $\hat{P}_{co}(Y,Z)$ coupled to a weighting process block 60 to provide weighted data elements $P_{co}(Y,Z)$. The weighted data elements are applied to circular data process block 62, which computes image reconstruction functions $f_{c1}(\vec{r})$ and $f_{co}(\vec{r})$. The functions $f_1(\vec{r})$, $f_{c1}(\vec{r})$ and $f_{co}(\vec{r})$ are respectively coupled to a summing device 64 to provide the function $f'(\vec{r})$. It will be understood that certain conventional functions performed by processor 22 are not necessary for understanding the invention, and are accordingly not shown.

Obviously, many other modifications and variations of the present invention are possible in light of the above teachings. It is therefore be understood that within the scope of the disclosed concept, the invention may be practiced otherwise than as specifically described.

What is claimed is:

1. In an imaging system wherein a source of cone beam radiation and a detector array are mounted for movement with respect to an object, a method for reconstructing an image of said object comprising the steps of:

establishing relative movement between said cone beam source and said object along a scan path comprising circular and linear components;

operating said cone beam source to irradiate said object during such movement to project cone beam data onto said detector array, said projected data comprising linear and circular data sets which respectively correspond to the linear and circular components of said scan path;

selecting a subset of data elements from said linear data set, each of said selected data elements being associated with a specified set of spatial parameters;

applying a Radon transform to each of said data elements in said selected subset to provide a first set of image reconstruction data;

selectively processing each of the data elements in the circular data set to provide a second set of image reconstruction data which collectively represents all the data elements in said circular data set; and combining said first and second sets of image reconstruction data to provide an image of said object.

2. The method of claim 1 wherein:

said specified spatial parameters define spatial regions only which are contained within a hypothetical sphere in the Radon space, and which are not intersected by a Radon shell defined by dimensions of said circular path and said cone beam.

3. The method of claim 2 wherein:

said first and second sets of image reconstruction data are generated by a process which includes filtering and backprojecting said cone beam data.

4. The method of claim 2 wherein said subset selecting step comprises applying a selection function to the data of said linear data set.

5. The method of claim 2 wherein:

said linear scan path component is tangent to said circular component, orthogonal to the plane thereof, and parallel to a Z-axis intersecting said plane at an origin O;

said detector array defines a selected plane, and a given one of said selected data elements in said subset, associated with a position $z_0$ along said linear scan path, lies along a line defined by the intersection of said detector plane and a plane associated with said given data element;

said given data element is identified by the spatial parameters $z_0$, $l$, $\Theta$ where $l$ is the length of a line normal to said line defined by said intersection, said normal line passing thorough said origin, and where $\Theta$ is the angle between said normal line and said Z-axis; and said spatial parameters of said given selected data element satisfy the relationship $2lz_0 \cos \Theta + z_0^2 \cos^2 \Theta - d^2 \sin^2 \Theta > 0$.

6. In an imaging system comprising a source of cone beam radiation and a detector, wherein relative movement is established between said source and an object along a scan path comprising respective linear and circular components to selectively project cone beam data onto said detector, said projected data comprising linear and circular data element sets respectively corresponding to said linear and circular scan path components, a method for reconstructing an image of said object comprising the steps of:

assigning a set of spatial parameters to each of said linear data elements;

selecting a given one of said linear data elements for a subset only if the spatial parameters of said given data element define a spatial region which is contained within a hypothetical sphere in Radon space, but is not contained within a toroidal space described by Radon shells respectively associated with said imaging system and defined by dimensions of said circular path and said cone beam;

applying a Radon transform to respective data elements of said subset to generate a first set of image reconstruction data; and generating a second set of image reconstruction data from said circular data element set and combining said first and second data sets to provide an image of said object.

7. The method of claim 6 wherein:

said linear scan path component is tangent to said circular component, and orthogonal to the plane thereof.

8. In an imaging system having an associated Z-axis and comprising a source of cone beam radiation and a detector defining a plane, wherein relative movement is established between said source and an object along a scan path comprising respective linear and circular components to selectively project cone beam data onto said detector, and wherein said projected data comprises linear and circular data element sets respectively corresponding to said linear and circular scan path components, a method of reconstructing an image of said object comprising the steps of:

determining the spatial parameters $z_0$, $l$, and $\Theta$ associated with each of said linear data elements wherein, for a given data element, $z_0$ indicates the position of said given data element along said linear scan path component, $l$ is the length of a line normal to a line defined by the intersection of said detector plane and a plane associated with said given data elements, and $\Theta$ is the angle between said normal line and said Z-axis;

selecting said given linear data element for a subset if its spatial parameters satisfy the relationship $2lz_0 \cos \Theta + z_0^2 \cos^2 \Theta - \alpha^2 \sin^2 \Theta > 0$;

generating a first set of image reconstruction data from said subset of linear data elements; and combining said first data set with a second set of image reconstruction data generated from said circular data set to provide an image of said object.

9. The method of claim 8 wherein:

A Radon transform is applied to respective data elements of said subset to generate said first set of image reconstruction data.

* * * * *